(12) United States Patent
Anderson et al.

(10) Patent No.: US 6,958,691 B1
(45) Date of Patent: Oct. 25, 2005

(54) MEDICAMENT DELIVERY SYSTEM

(75) Inventors: Gregor John McLennan Anderson, Ware (GB); Stanley George Bonney, Ware (GB); Anthony Patrick Jones, Ware (GB); Duncan Robertson, Perth (AU)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/089,760

(22) PCT Filed: Sep. 22, 2000

(86) PCT No.: PCT/EP00/09291

§ 371 (c)(1),
(2), (4) Date: Apr. 2, 2002

(87) PCT Pub. No.: WO01/24690

PCT Pub. Date: Apr. 12, 2001

(30) Foreign Application Priority Data

| Oct. 1, 1999 | (GB) | .................................... 9923273 |
| May 9, 2000 | (GB) | .................................... 0011029 |
| Aug. 22, 2000 | (GB) | .................................... 0020541 |

(51) Int. Cl.$^7$ ............................................. G08B 1/08
(52) U.S. Cl. ........................ 340/539.12; 128/200.14; 340/573.1; 705/2
(58) Field of Search ................ 340/573.1, 539.11, 340/539.12, 539.13; 705/2, 3; 128/200.14, 128/200.21

(56) References Cited

U.S. PATENT DOCUMENTS

| 5,338,157 | A |   | 8/1994 | Blomquist | |
| 5,363,842 | A | * | 11/1994 | Meshelevich et al. | . 128/200.14 |
| 5,544,661 | A | * | 8/1996 | Davis et al. | ........... 128/200.14 |
| 5,809,997 | A | * | 9/1998 | Wolf | ..................... 128/200.23 |
| 5,822,715 | A | * | 10/1998 | Worthington et al. | ......... 702/19 |
| 5,924,074 | A |   | 7/1999 | Evans | |
| 6,119,684 | A | * | 9/2000 | Nohl et al. | ............ 128/200.14 |
| 6,142,149 | A | * | 11/2000 | Steen | .................... 128/204.23 |
| 6,202,642 | B1 | * | 3/2001 | McKinnon et al. | ..... 128/200.23 |
| 6,435,175 | B1 | * | 8/2002 | Stenzler | ................. 128/200.14 |

FOREIGN PATENT DOCUMENTS

| WO | WO 9910829 A | 3/1999 |
| WO | WO 9941682 A | 8/1999 |

* cited by examiner

*Primary Examiner*—Thomas Mullen
(74) *Attorney, Agent, or Firm*—James P. Riek (57) ABSTRACT

There is provided a system for the delivery of medicament comprising a medicament container; a dispensing mechanism for dispensing medicament from the medicament container; an electronic data management system; and a communicator for wireless communication with a network computer system to enable communication of data between the network computer system and the electronic data management system. The electronic data management system comprises a memory for storage of data; a microprocessor for performing operations on the data; and a transmitter for transmitting a signal relating to the data or the outcome of an operation on the data.

33 Claims, 5 Drawing Sheets

MEDICAMENT DELIVERY SYSTEM

CROSS-REFERENCE TO RELATED APPLICATIONS

This application is filed pursuant to 35 USC 371 as a United States National Phase Application of Ser. No. PCT/EP00/09291 filed 22 Sep. 2000, which claims priority from GB 9923272.8 filed 1 Oct. 1999; GB 0011029 filed 9 May 2000; and GB 00205419.9 filed 22 Aug. 2000, each in the United Kingdom.

BACKGROUND OF THE INVENTION

Field of the Invention

The present invention relates to a system for the delivery of medicament having an electronic data management system. The system is capable of wireless communication with an entrypoint to a network computer system to enable communication of data between the network computer system and the electronic data management system.

DESCRIPTION OF THE RELATED ART

It is common prescribing practice for a doctor to prescribe a patient with medicament in a medicament dispenser together with instructions for patient administration of the medicament according to a defined treatment regimen. The patient typically therefore, receives instructions relating to the correct use of the dispenser together with recommended dosing amounts, dose intervals and treatment period. The patient is then trusted to follow the treatment regimen as set by the doctor.

A limitation associated with this practice is that the treatment regimen is set at the time of prescription and can therefore not account for changes in the patient's condition over the treatment period. A further limitation associated with this practice is that the onus is on the patient to comply with the doctor's instructions. Occasionally, patients will forget to take the medicament or will vary the treatment regimen in an unpredictable manner with possible consequences for the success of the treatment.

A variation on the above-described prescribing practice involves the use by a patient of a diagnostic device which enables data relating to their medical condition to be gathered on a regular basis. This data may for example, be collected prior to administration of any medicament and a correct dose amount calculated on the basis of the diagnostic data. An example of this practice would be that of a diabetic who checks their blood-sugar levels in order to calculate a required dose of insulin.

In developments of the practice variation, the diagnostic device may be integrated with the delivery system. Information relating to the patient's condition and usage of the dispenser may thus be displayed to the patient to enable the better management of their medical condition. The information may further be stored in a memory such that it may be recalled at a later time to enable historic analysis of the progress of the condition and effect of the treatment. Dispensers employing electronic data management systems have been proposed for this purpose.

U.S. Pat. No. 5,363,842 describes an inhalation device for use in delivering inhalable medicament. The device enables data relating to the patient's breathing pattern to be collected, analysed and displayed to the patient. The data is stored in a memory for download to a workstation at the clinic.

WO99/35588 describes a method for managing the administration of medicine and in particular, monitoring patient compliance with a prescribed treatment regimen. The method relies on input of patient data to a central computer workstation. The central computer workstation calculates and transmits dosage data to a dispensing device via a communications link. The dispensing device delivers drug in accord with the dosage data.

BRIEF SUMMARY OF THE INVENTION

The Applicants have now developed an improved system for the delivery of medicament which employs an electronic data management system. The system is capable of wireless communication with a network computer system to enable communication of data between the network computer system and the electronic data management system. The system therefore, provides the advantage of enabling data transfer with a network of computers, which network can be made accessible to diverse remote information sources, which may in turn be networked together for cross-transfer of data. The patient therefore, has ready access to diverse, possibly inter-connected, remote information sources capable of providing disease management information. In turn, the system can feed information, such as compliance information, back to any remote information source having access to the network computer system. The system can also be integrated with a healthcare management system for remote prescribing or remote variation or control of the prescribing regimen. The healthcare management system will typically be under the control of a healthcare professional such as a doctor.

According to one aspect of the present invention there is provided a system for the delivery of medicament comprising a medicament container; a dispensing mechanism for dispensing medicament from the medicament container; an electronic data management system; and a communicator for wireless communication with a network computer system to enable transfer of data between the network computer system and the electronic data management system.

The elements of the system herein will in one preferred embodiment be comprised within a single device having medicament delivery, electronic data management and communications capability. The device is preferably a portable or hand held device.

In another preferred embodiment, the electronic data management and communications aspects of the system will be comprised as a distinct control unit which is associated with the medicament delivery aspects of the system. The control unit may for example form a snap-fit module which receives or is receivable by a separate medicament delivery device.

The network computer system is typically located at, and under the control of, a healthcare provider or manager such as a doctor's practice, a hospital or healthcare management centre. It is an advantage of the system herein, that the network computer system may be located geographically distant from the patient but be wirelessly accessible to the patient via the system of the present invention.

The electronic data management system comprises a memory for storage of data; a microprocessor for performing operations on said data; and a transmitter for transmitting a signal relating to the data or the outcome of an operation on the data.

Either the network computer system or the communicator may initiate data transfer. Preferably, the communicator enables two-way transfer of data between the network computer system and the electronic data management system.

Suitably, the data is communicable between the network computer system and the electronic data management system in encrypted form. All suitable methods of encryption or partial encryption are envisaged. Password protection may also be employed. Other methods of ensuring data security are envisaged including the use of systems reliant on the use of secure token codes.

Suitably, the communicator employs radiofrequency or optical (e.g. infra red or ultra violet) signals.

In one aspect, the communicator communicates with the network computer system via a gateway thereto. Communication will typically involve the use of a suitable communications protocol.

In another aspect, the system (device) is provided with an embedded network server to enable it to be comprises directly within the network system, typically using IP protocol. The embedded network server will have hardware and software components and for example comprise an HTTP (web) server, an FTP (file) server or an SMTP (main) server. The embedded network server will typically be provided with a unique network address such as a web-site address, an e-mail address or a file transfer protocol address. The so-enabled system (device) may also have the capability to form local area networks with other similarly enabled systems (devices) to enable local transfer of data therebetween.

Suitably, the communicator communicates with network computer system via a second communications device. The second communications device may itself comprise an embedded web server. Preferably, the second communications device is a telecommunications device, more preferably a cellular phone or pager. Preferably, the communicator communicates with the second communications device using spread spectrum radiofrequency signals. A suitable spread spectrum protocol is the Bluetooth (trade mark) standard which employs rapid (e.g. 1600 times a second) hopping between plural frequencies (e.g. 79 different frequencies). The protocol may further employ multiple sending of data bits (e.g. sending in triplicate) to reduce the effect of interference.

In another aspect, the communicator communicates with the second communications device using an infra red data communications standard (e.g. IrDA).

In one aspect, the network computer system comprises a public access network computer system. The Internet is one suitable example of a public access network computer system, wherein the entrypoint thereto is typically managed by an Internet service provider. The public access network computer system may also form part of a telecommunications system, which may itself be either a traditional copper wire system, a cellular system or an optical or microwave network.

In another aspect, the network computer system comprises a private access network computer system typically comprising a private entrypoint system. The private access network system may for example, comprise an intranet or extranet which may for example, be maintained by a health service provider or medicament manufacturer. The private access network system may for example include password protection; a firewall; and suitable encryption means.

Suitably, different levels of access authorisation to the network computer system will be provided to different authorised users. Example of authorised users may include the patient, a healthcare professional such as a doctor or nurse, a pharmacist, an emergency assistance provider, a research professional, a database manager and any combinations thereof.

Suitably, the communicator enables communication with a user-specific network address in the network computer system. The user-specific network address may be selected from the group consisting of a web-site address, an e-mail address and a file transfer protocol address. The network address may be pre-assigned or it may be dynamically assigned at the time of communication.

Suitably, the user-specific network address is accessibly to a remote information source such that information from said remote information source can be made available thereto. More preferably, information from the user-specific network address can be made available to the remote information source.

In one aspect, the remote information source is a medicament prescriber, for example a doctor's practice. Information transferred from the medicament prescriber may thus, comprise changes to prescription details, prescription updates or training information. Information transferred to the medicament prescriber may comprise compliance information, that is to say information relating to the patient's compliance with a set-prescribing programme. Patient performance information relating for example, to patient-collected diagnostic data may also be transferred to the medicament prescriber. Where the dispenser is an inhaler for dispensing medicament for the relief of respiratory disorders examples of such diagnostic data would include breath cycle data or peak flow data.

In another aspect, the remote information source is a pharmacy. Information transferred from the pharmacy may thus, comprise information relating to the medicament product. Information sent to the pharmacy may thus include prescription requests, which have been remotely pre-authorized by the medicament prescriber.

In a further aspect, the remote information source is an emergency assistance provider, for example a hospital accident and emergency service or an emergency helpline or switchboard. The information may thus, comprise a distress or emergency assist signal which requests emergency assistance.

In a further aspect, the remote information source is a manufacturer of medicament or medicament delivery systems. Information transferred to the system may thus, comprise product update information. The system may also be configured to feed information back to the manufacturer relating to system performance.

In a further aspect, the remote information source is a research establishment. In a clinical trails situation, information may thus be transferred relating to the trials protocol and information relating to patient compliance fed back to the research establishment.

In a further aspect, the remote information source is an environmental monitoring station. Information relating to weather, pollen counts and pollution levels may thus be made accessible to the system.

The communicator may also enable communication with a public-access network address such as a public web-site on the Internet.

Suitably, the system additionally comprises a wired or wireless datalink for linking to a local data store such as a personal computer or set-top box to enable communication of data between the local data store and the microprocessor. Preferably, the datalink comprises an infrared emitter and sensor.

Suitably, the system additionally comprises a data input system for use input of data to the electronic data management system. More preferably, the data input system comprises a man machine interface (MMI) preferably selected from a keypad, voice recognition interface, graphical user interface (GUI) or biometrics interface.

Suitably, the system additionally comprises a display for display of data from the electronic data management system to the user. The display may for example, comprise a screen such as an LED or LCD screen.

Suitably, the electronic data management system includes a predictive algorithm or look-up table for calculating the optimum amount of medicament to dispense.

Suitably, the memory includes a dose memory for storing dosage data and reference is made to the dose memory in calculating the optimum amount of medicament to dispense.

Suitably, the system additionally comprises a selector for selecting the amount of medicament to dispense from said dispensing mechanism. The selector may thus be employed to vary the medicament dose for dispensing from the dispensing mechanism.

In one aspect, the selector is manually operable.

In another aspect, the selector is operable in response to a signal from the transmitter.

Suitably, the selector comprises a timing mechanism for varying the time interval of actuation of the dispensing mechanism.

Alternatively, the selector comprises a metering mechanism between the medicament container and the dispensing mechanism for metering a variable quantity of medicament for dispensing.

Alternatively, the selector comprises a multiple-fire mechanism for multiple actuation of the dispensing mechanism, wherein each actuation releases a portion of the optimum amount of medicament. Successive actuations may be pulsed, for example such that the time intervals between actuations may be based on arithmetic or geometric progressions.

Suitably, the system additionally comprises a detector for detecting dispensing from the medicament container, wherein said detector communicates dispensing data to the electronic data management system.

Suitably, the system additionally comprises a geographic positioning system such as a global positioning system or a system which relies on the use of multiple communications signals and a triangulation algorithm.

In one aspect, the system is suitable for the delivery of inhalable medicament and additionally comprises a sensor which senses the breath of a user, wherein the sensor communicates breath data to the electronic data management system.

In one aspect, the sensor comprises a breath-movable element which is movable in response to the breath of a patient. More preferably, the breath-movable element is selected from the group consisting of a vane, a sail, a piston and an impeller.

In another aspect, the sensor comprises a pressure sensor for sensing the pressure profile associated with the breath of a user.

In a further aspect, the sensor comprises an airflow sensor for sensing the airflow profile associated with the breath of a user.

In a further aspect, the sensor comprises a temperature sensor for sensing the temperature profile associated with the breath of a user. The temperature of the inhaled and exhaled part of the breath cycle varies and may, thus, be used as a measurement tool.

In a further aspect, the sensor comprises a moisture sensor for sensing the moisture profile associated with the breath of a user. The moisture content of the inhaled and exhaled part of the breath cycle varies and this also may be used as a measurement tool.

In a further aspect, the sensor comprises a gas sensor for sensing the oxygen or carbon dioxide profile associated with the breath of a user. The chemical profile of the inhaled and exhaled part of the breath cycle varies and this further may be used as a measurement tool.

Suitably, the breath data includes breath cycle data or peak flow data.

Suitably, the system additionally comprises an actuator for actuating the dispensing mechanism, said actuator being actuable in response to a trigger signal from the transmitter.

Suitably, the electronic data management system includes a predictive algorithm or look-up table for deriving from the breath data when to transmit the trigger signal. For example, a real-time analysis of the patient breath waveform may be made and the trigger point derived by reference to that analysed waveform.

In one preferred aspect, the medicament container is an aerosol container and the dispensing mechanism is an aerosol valve.

In another preferred aspect, the medicament container is a dry-powder container, that is to say a container suitable for containing medicament in dry-powder form.

Suitably, the actuator comprises an energy store for storing energy which energy is releasable to actuate the dispensing mechanism of the medicament container. The energy store comprises in preferred aspects, a biasable resilient member such as a spring, a source of compressed fluid such as a canister of compressed gas or a battery. Chemical energy sources are also suitable and might include chemical propellant or ignition mixtures. Other sources might include physical explosives such as liquefied or solidified gas in a canister which burst when heated or exposed to the atmosphere.

The system may additionally comprise a safety mechanism to prevent unintended multiple actuations of the actuator. The patient is thereby protected from inadvertently receiving multiple doses of medicament in a situation where they take a number of short rapid breaths. More preferably, the safety mechanism imposes a time delay between successive actuations of the actuator. The time delay is typically of the order of from three to thirty seconds.

An actuation counter which can be mechanical or electronic may be provided to the system.

A medicament dispensing counter, such as a dose counter, may be provided to the system. This may be mechanical or electronic. The counter may be coupled to a visual display to provide feedback to the patient as to amount of drug released or remaining in the container.

A manual override can be provided to the system for use in the event of emergency or system failure.

According to another aspect of the present invention there is provided a data communicator for use with a medicament dispenser comprising an electronic data management system; a communicator for communicating wirelessly with a network computer system to enable communication of data between the network computer system and the microprocessor; and a coupling mechanism for coupling the data communicator to the medicament dispenser.

The electronic data management system comprises a memory for storage of data; a microprocessor for performing operations on said data; and a transmitter for transmitting a signal relating to the data or the outcome of an operation on the data. The memory may comprise a non-volatile memory chip (e.g. an EEPROM or FLASH memory chip) which is capable of storing data when the electronic data management system is turned off.

According to another aspect of the present invention there is provided a kit of parts comprising a data communicator as described above and a medicament dispenser comprising a medicament container; and a dispensing mechanism for dispensing medicament from the medicament container.

The data communicator may for example, be mechanically coupled to the medicament dispenser by any suitable mechanical mechanism including grip mechanisms and snap-fit mechanisms. In a preferred aspect, the data communicator forms a snap-in module and the dispenser is shaped to be receivable by or for receipt of the module.

In aspects, the data communicator or any distinct device aspects of the system may be adapted to be worn on the body of the user. Examples would include belt attachable devices, devices in the form of watches for wrist or leg attachment and devices attachable as jewellery. Suitable body attachment means will be incorporated as required.

According to further aspects of the present invention there are provided methods for use of the system herein and software for the implementation thereof.

BRIEF DESCRIPTION OF THE SEVERAL VIEWS OF THE INVENTION

Embodiments of systems according to the invention will now be described with reference to the accompanying drawings in which.

DETAILED DESCRIPTION OF THE INVENTION

Figure 1:
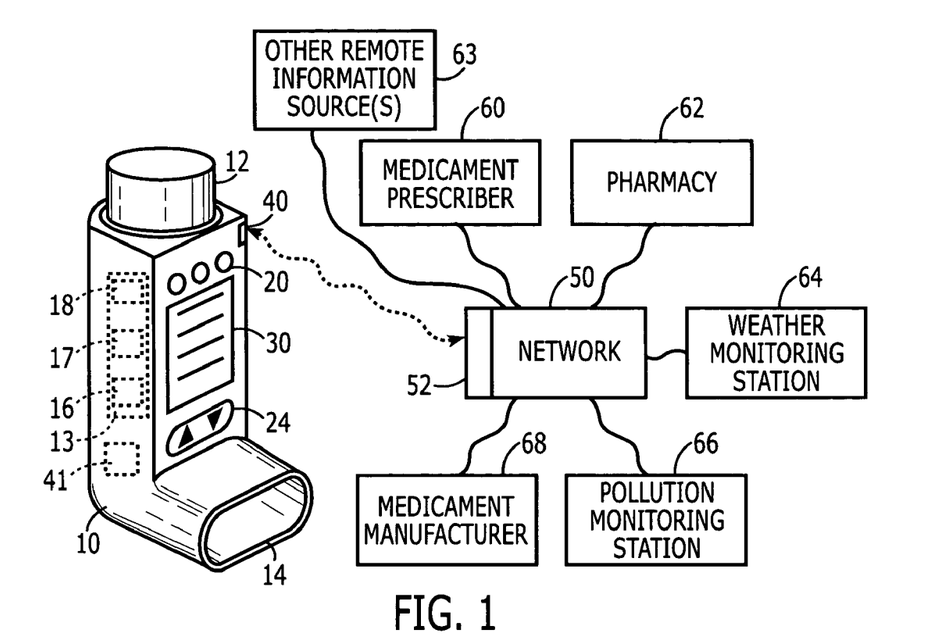
FIG. 1 is a schematic representation of a first system in accord with the present invention.

FIG. 1 shows a standard-form metered dose inhaler for the delivery of inhalable medicament comprising a tubular housing 10 in which an aerosol container 12 is located. The housing is open at one end (which will hereinafter be considered to be the top of the device for convenience of description) and is closed at the other. A dispensing outlet 14 leads laterally from the closed end of the housing 10. In the embodiment illustrated, the outlet 14 is in the form of a mouthpiece intended for insertion into the mouth of the patient but it may, if desired, be designed as a nozzle for insertion into the patient's nostril.

The aerosol container 12 is located in the housing 10 so that one end protrudes from the open top of the housing 10. The aerosol container 12 has an outlet valve stem (for example, 131 in FIG. 2) at one end which connects with a support (not shown) in the housing 10. To dispense the dose, the protruding portion of the aerosol container 12 is depressed to move the container 12 relative to the valve stem to open the valve and dispense medicament into the outlet 14 from which it can be inhaled by a patient.

Figure 2:
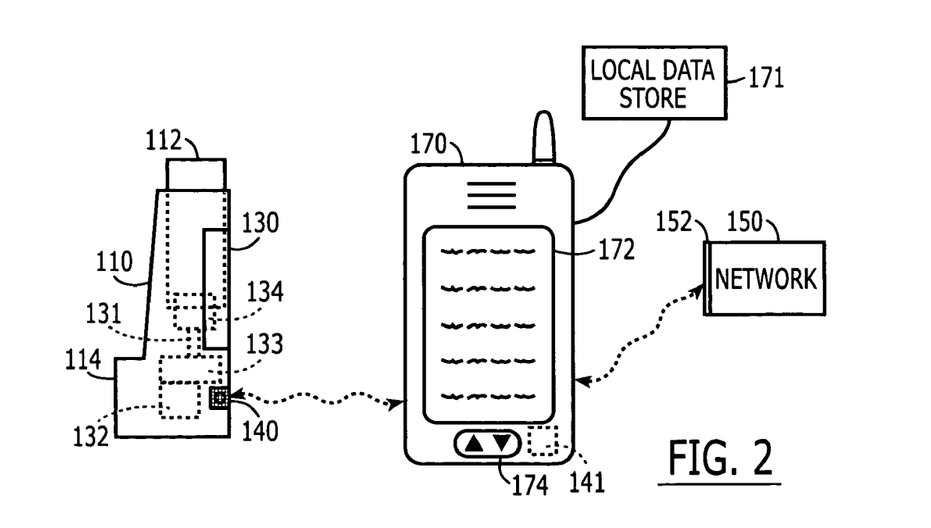
FIG. 2 is a schematic representation of a second system in accord with the present invention.

In an alternative form, as alternatively depicted in FIG. 2, the system is suitable for the delivery of inhalable medicament and additionally comprises a sensor 132, which senses the breath of a user, wherein the sensor communicates breath data to the electronic data management system. In one aspect, the sensor comprises a breath-moveable element which is movable in response to the breath of a patient. More preferably, the breath-movable element is selected from the group consisting of a vane, a sail, a piston and an impeller. In another aspect, the sensor comprises a pressure sensor for sensing the pressure profile associated with the breath of a user. In a further aspect, the sensor comprises an airflow sensor for sensing the airflow profile associated with the breath of a user. In a further aspect, the sensor comprises a temperature sensor for sensing the temperature profile associated with the breath of a user. The temperature of the inhaled and exhaled part of the breath cycle varies and may, thus, be used as a measurement tool. In a further aspect, the sensor comprises a moisture sensor for sensing the moisture profile associated with the breath of a user. the moisture content of the inhaled and exhaled part of the breath cycle varies and this also may be used as a measurement tool. In a further aspect, the sensor comprises a gas sensor for sensing the oxygen or carbon dioxide profile associated with the breath of a user. The chemical profile of the inhaled and exhaled part of the breath cycle varies and this further may be used as a measurement tool. Suitably, the breath data includes breath cycle data or peak flow data.

Suitably, the system additionally comprises an actuator 133 for actuating the dispensing mechanism, said actuator being actuable in response to a trigger signal from the transmitter. The actuator triggers a mechanism leading to the release of medicament from aerosol valve 134.

The dispenser includes an electronic data management system 13 in the form of an integrated circuit preferably integrated into one or more integrated circuit chips and comprised with the housing . The electronic data management system 13 comprises a memory 16 for storage of data; a microprocessor 17 for performing operations on said data; and a transmitter 18 for transmitting a signal relating to the data or the outcome of an operation on the data. The user may access the electronic data management system by use of push-buttons 20 and toggle menu-button 24. Display 30 allows for display of menu choices and data from the electronic data management system. The dispenser communicates via communications transceiver (also referred to as "communicator") 40 to network computer system 50, through a gateway 52. The network computer system 50 comprises a secure extranet computer system. Remote information sources 60, 62, 63, 64, 66, 68 also have access to the extranet. In more detail, the remote information sources comprise a medicament prescriber 60, a pharmacy 62, a weather monitoring station 64, a pollution monitoring station 66 and a medicament manufacturer 68. Other remote information source(s) 63 include, but are not limited to an emergency assistance provider and a research establishment. Two-way data transfer is possible between the electronic data management system and the network computer system 50 via the communications transceiver 40. Information transfer is thus possible between the electronic data management system and any of the remote information sources 60, 62, 63 64, 66, 68. Information received from any of the remote information sources 60, 62, 63, 64, 66, 68 may be utilised by the electronic data management system to vary the recommended medicament dose for delivery to the patient.

FIG. 2 shows a variation of the system of FIG. 1. The system comprises standard-form metered dose inhaler for the delivery of inhalable medicament comprising tubular housing 110, an aerosol container 112, a valve stem 131, an aerosol valve 134, and dispensing outlet 114. Operation of the inhaler is as described above with reference to FIG. 1.

The dispenser includes an electronic data management and communications system 140 comprised within the housing 110. Display 130 allows for limited display data from the electronic data management system. The dispenser readily communicates via chip 140 to palmtop computer 170. The communication is via spread spectrum radiofrequency signals operable over a relatively short range (e.g. up to ten meters). The palmtop computer 170 has a more sophisticated display 172 including a graphical user interface comprising menu-entry screens from which selections may be made using toggle menu-bottom 174.

The user accesses the electronic data management system of the dispenser 110 through the palmtop computer 170. The electronic data management system interacts with the palmtop computer via communicator 140. The palmtop computer 170 itself can communicate through a telecommunications link with network computer system 150, through a gateway 152. The network computer system 150 comprises a secure extranet computer system. As in FIG. 1, remote information sources may also have access to the extranet. Two-way data transfer is possible between the electronic data management system and the network computer system 150 via the communications links with the palmtop computer 170. Information transfer is thus possible between the electronic data management system 140, palmtop computer 170 and any of the remote information sources. The system may additionally comprise a geographic positioning system, depicted as optional component 141 (also depicted as 41 in FIG. 1), such as a global positioning system or a system which relies on the use of multiple communications signals and a triangulation algorithm.

Figure 3:
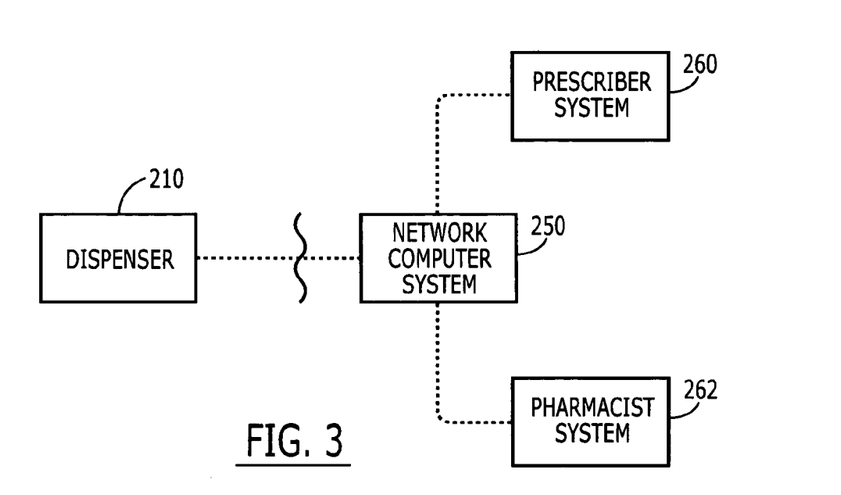
FIGS. 3 and 4 are schematic representations of third and fourth systems in accord with the present invention in which the electronic data management system integrates with a system for electronic prescription of medicament.

FIG. 3 shows a system herein in which patient electronic data management system in dispenser 210 communicates wirelessly with geographically distant network computer system 250. The network computer system 250 is itself accessible (i.e., wirelessly or via a modem link) by the system of a medicament prescriber 260 (e.g. a doctor's surgery system) and by the system of a pharmacist 262.

The system of FIG. 3 may be employed in the remote assessment of a patient and electronic prescribing therefor as follows. The patient data management system in dispenser 210 communicates data relating to the medical condition of the patient to the network computer system 250. The medicament prescriber 260 accesses this data e.g. wirelessly by use of a palmtop communications and data management device and makes a judgement as to prescription needs. If a new prescription is needed the prescriber sends a 'prescription authorisation' signal to the network computer system 250. The pharmacist 262 then accesses the network computer system to receive the 'prescription authorisation' signal which authorises them to make up the prescription for the patient.

Figure 4:
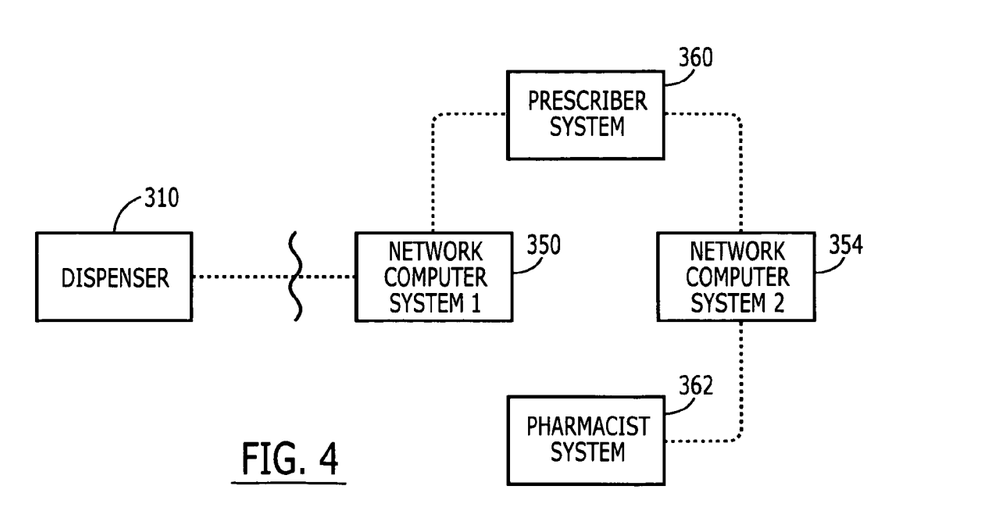

The system of FIG. 4 is a variation of the system of FIG. 3 in which patient electronic data management system in dispenser 310 communicates wirelessly with geographically distant network computer system 350. The network computer system 350 is itself accessible by the system of a medicament prescriber 360 (e.g. via a modem-enabled personal computer of a doctor). The prescriber system 360 may also access second network computer system 354 which is accessible by the system of a pharmacist 362. In an alternative herein, the second computer system 354 may be integral with the system of the pharmacist 362 or be a dedicated secure prescription system accessible only to the prescriber and the pharmacist.

The system of FIG. 4 is employed in the remote assessment of a patient and electronic prescribing therefor as follows. The patient data management system in dispenser 310 communicates data relating to the medical condition of the patient to the network computer system 350. The medicament prescriber 360 wirelessly accesses this data and makes a judgement as to prescription needs. If a new prescription is needed the prescriber sends a 'prescription authorisation' signal to the second network computer system 354. The pharmacist 362 then accesses the network computer system to receive the 'prescription authorisation' signal which authorises the pharmacist to make up the prescription for the patient.

Figure 5:
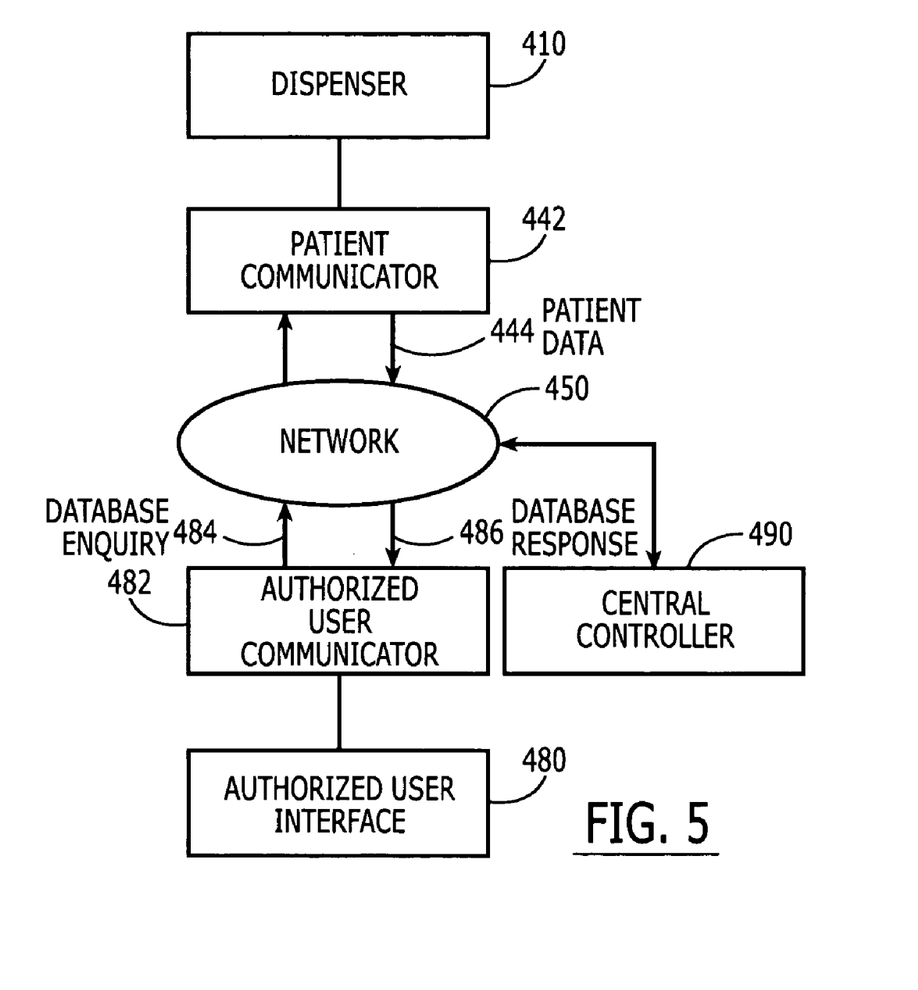
FIG. 5 is a system diagram of a further system in accord with the present invention.

FIG. 5 shows a representative system herein comprising an electronic patient data management system in dispenser 410 which would be under the control of the patient. Associated with the patient electronic data management system in dispenser 410 there is a patient communicator 442 which is capable of wireless communication with a network computer system 450. The system also comprises an authorised user interface 480 having associated authorised user communicator 482 which is capable of communicating with the network computer system 450. Central controller unit 490 is in two-way communication with the network computer system 450.

The system of FIG. 5 is shown in patient 'data upload mode' wherein patient data 444 is wirelessly communicated from the patient data management system to the network. It may be appreciated that any patient can also communicate requests for data to the network 450 and receive responses thereto via the patient communicator 442 and patient data management system. The system is also shown in authorised user 'enquiry mode' in which a database enquiry 484 is communicated to the network computer system 450 and a response received 486 via the authorised user communicator 482 to the authorised user interface 480.

Figure 6:
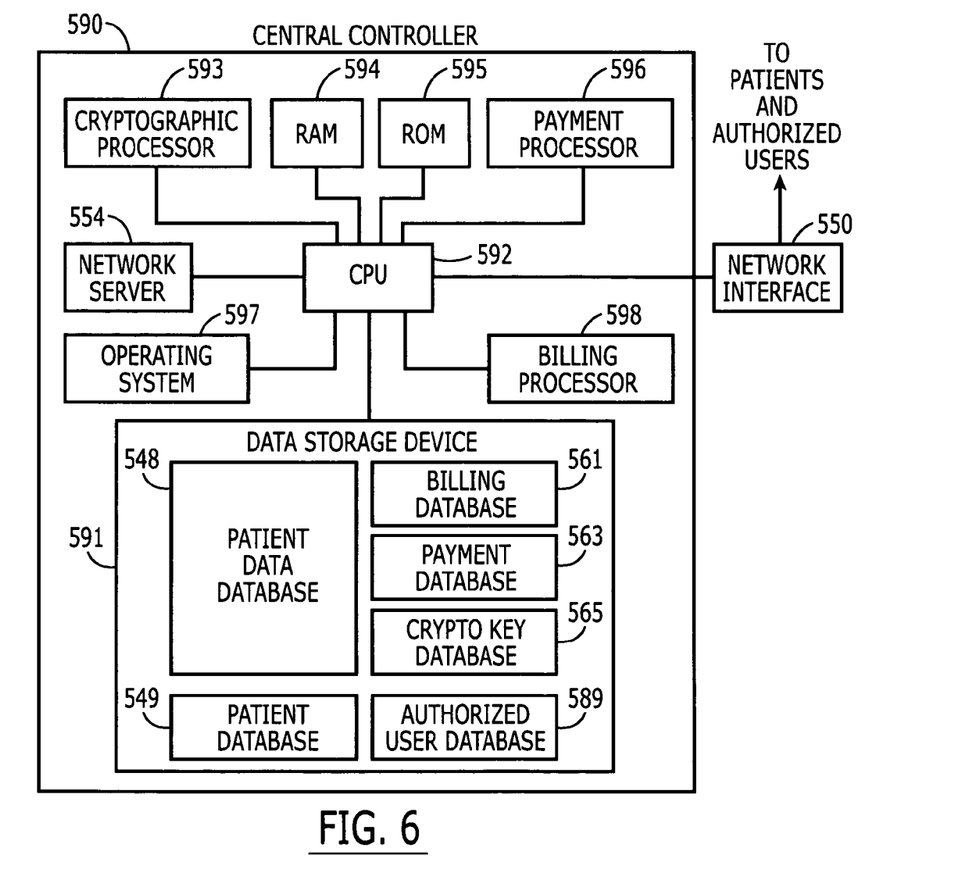
FIG. 6 is a system diagram of a central controller unit for use in accord with the present invention.

FIG. 6 shows the structure of the central controller 590 in more detail. The central controller includes a data storage device 591, central processor (CPU) 592, cryptographic processor 593, RAM 594, ROM 595, payment processor 596, operating system 597 and billing processor 598.

The components of the central controller 590 must be selected to be capable of handling sufficiently large volumes of data. The data storage devices, processors and operating system and other components may be selected from those commercially available.

The data storage device 591 is partitioned to include plural databases. The databases comprise a patient data database 548 which comprises data communicated from the patient electronic data manager; a patient database 549 which includes patient details such as name, address and possibly medical history; an authorised user database 589 which includes details of authorised users of the system; a billing database 561 for use in billing authorised users on retrieval of data; a payment database 563 for use in payment of other authorised users in return for data provided; and a crypto key database 565 comprising encryption information.

It will be appreciated that various parts of the system are designed to co-operate with each other in use. For example, the cryptographic processor 593 will access the crypto key database 565 to enable performance of user authentication. Together these crypto elements may form a secure access gateway to the patient data database.

Figure 7:
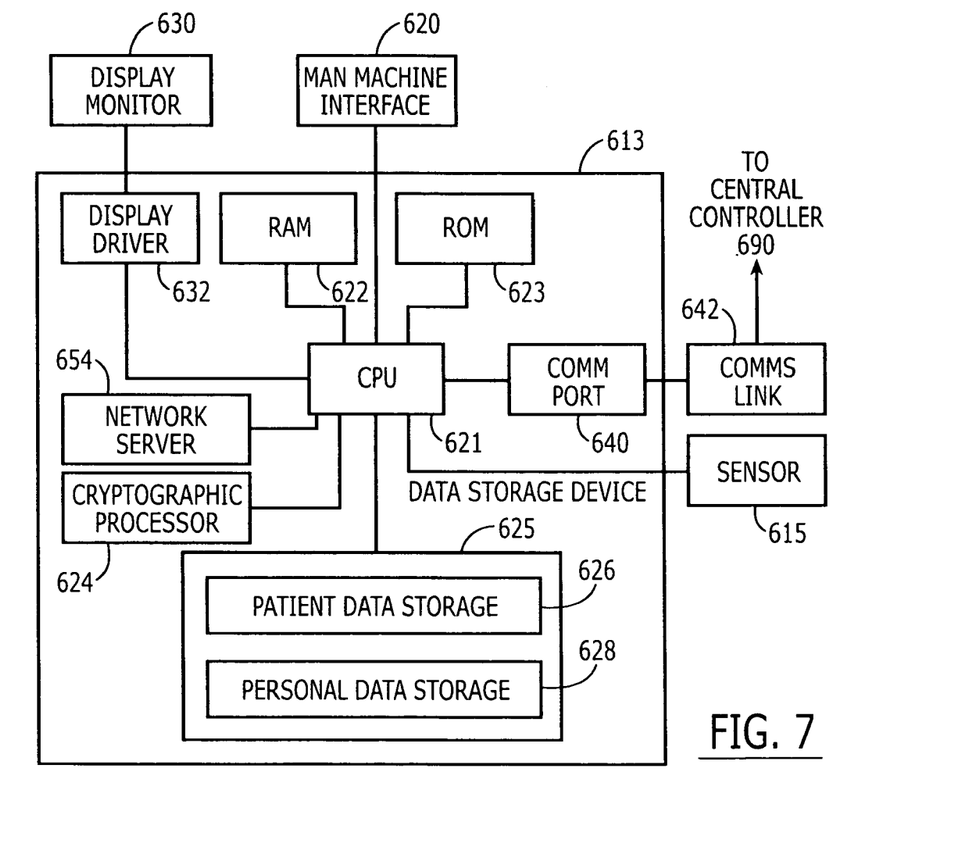
FIG. 7 is a system diagram of a patient electronic data manager for use in accord with the present invention.

FIG. 7 shows a patient electronic data manager 613 comprised with a respiratory drug delivery system. The electronic data manager 613 comprises a central processor unit (CPU) 621; RAM 622; ROM 623 and a cryptographic processor 624. The CPU 621 receives patient data from sensor 615 which may for example be a breath sensor or a sensor detecting actuation of the respiratory drug delivery system. The received data is storable in data storage device 625 which includes two databases, one for storage of patient medical data 626 and one for storage of personal patient data 628. The CPU 621 is associated with man machine interface 620 for receipt of patient input commands and display driver 632 and display 630 for display of information to the patient. The CPU 621 is further associated with communications port 640 which links via wireless communications link 642 to the central controller 690 of a network computer system (not shown).

It will be appreciated that the basic structure of the patient data management system 613 of FIG. 7 can act as an authorised data communicator for making enquiry requests to the databases on the network computer system and receiving responses therefrom. It will also be appreciated that the structure of the patient data management system could be adapted by removal of the sensor 615 to form a non-patient authorised data communicator which would not be comprised within a respiratory drug delivery system.

The system of the invention is one aspect suitable for dispensing medicament for the treatment of respiratory disorders such as disorders of the lungs and bronchial tracts including asthma and chronic obstructive pulmonary disorder (COPD).

Appropriate medicaments may thus be selected from, for example, analgesics, e.g., codeine, dihydromorphine, ergotamine, fentanyl or morphine; anginal preparations, e.g., diltiazem; antiallergics, e.g., cromoglycate (e.g., as the sodium salt), ketotifen or nedocromil (e.g., as the sodium salt); antiinfectives e.g., cephalosporins, penicillins, streptomycin, sulphonamides, tetracyclines and pentamidine; antihistamines, e.g., methapyrilene; anti-inflammatories, e.g., beclomethasone (e.g., as the dipropionate ester), fluticasone (e.g., as the propionate ester), flunisolide, budesonide, rofleponide, mometasone e.g., as the furoate ester), ciclesonide, triamcinolone (e.g., as the acetonide) or 6α, 9α-difluoro-11β-hydroxy-16α-methyl-3-oxo-17α-propionyloxyandrosta-1,4-diene-17β-carbothioic acid S-(2-oxotetrahydro-furan-3-yl) ester; antitussives, e.g., noscapine; bronchodilators, e.g., albuterol (e.g., as free base or sulphate), salmeterol (e.g., as xinafoate), ephedrine, adrenaline, fenoterol (e.g., as hydrobromide), formoterol (e.g., as fumarate), isoprenaline, metaproterenol, phenylephrine, phenylpropanolamine, pirbuterol (e.g., as acetate), reproterol (e.g., as hydrochloride), rimiterol, terbutaline (e.g., as sulphate), isoetharine, tulobuterol or 4-hydroxy-7-[2-[[2-[[3-(2-phenylethoxy)propyl]sulfonyl]ethyl]amino]ethyl-2(3H)-benzothiazolone; adenosine 2a agonists, e.g., 2R,3R,4S,5R)-2-[6-Amino-2-(1S-hydroxymethyl-2-phenyl-ethylamino)-purin-9-yl]-5-(2-ethyl-2H-tetrazol-5-yl)-tetrahydro-furan-3,4-diol (e.g., as maleate); $\alpha_4$ integrin inhibitors e.g., (2S)-3-[4-({[4-(aminocarbonyl)-1-piperidinyl]carbonyl}oxy) phenyl]-2-[((2S)-4-methyl-2-{[2-(2-methylphenoxy)acetyl] amino}pentanoyl)amino] propanoic acid (e.g., as free acid or potassium salt), diuretics, e.g., amiloride; anticholinergics, e.g., ipratropium (e.g., as bromide), tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon; vaccines, diagnostics, and gene therapies. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament.

Preferred medicaments are selected from albuterol, salmeterol, fluticasone propionate and beclomethasone dipropionate and salts or solvates thereof, e.g., the sulphate of albuterol and the xinafoate of salmeterol.

Medicaments can also be delivered in combinations. Preferred formulations containing combinations of active ingredients contain salbutamol (e.g., as the free base or the sulphate salt) or salmeterol (e.g., as the xinafoate salt) or formoterol (e.g., as the fumarate salt) in combination with an anti-inflammatory steroid such as a beclomethasone ester (e.g., the dipropionate) or a fluticasone ester (e.g., the propionate) or budesonide. A particularly preferred combination is a combination of fluticasone propionate and salmeterol, or a salt thereof (particularly the xinafoate salt). A further combination of particular interest is budesonide and formoterol (e.g. as the fumarate salt).

It will be understood that the present disclosure is for the purpose of illustration only and the invention extends to modifications, variations and improvements thereto.

The application of which this description and claims form part may be used as a basis for priority in respect of any subsequent application. The claims of such subsequent application may be directed to any feature or combination of features described thereon. They may take the form of product, method or use claims and may include, by way of example and without limitation, one or more of the following claims:

What is claimed is:

1. A portable device for the delivery of medicament comprising
   a housing;
   received by said housing, a medicament container;
   associated with said medicament container, a dispensing mechanism for dispensing medicament from the medicament container;
   said portable device further comprising an electronic data management system comprising
      a memory for storage of data concerning use of said portable device;
      a microprocessor for performing operations on said data; and
      a transmitter for transmitting a signal relating to the data or the outcome of an operation on the data; and
   associated with the electronic data management system, a communicator for wireless communication with a remote network computer system to enable two-way transfer of data between the network computer system and the electronic data management system
   wherein the data is communicable between the network computer system and the electronic data management system in encrypted form.

2. A portable device for the delivery of medicament comprising
   a housing;
   received by said housing, a medicament container;
   associated with said medicament container, a dispensing mechanism for dispensing medicament from the medicament container;

said portable device further comprising, an electronic data management system comprising
    a memory for storage of data concerning use of said portable device;
    a microprocessor for performing operations on said data; and
    a transmitter for transmitting a signal relating to the data or the outcome of an operation on the data; and
associated with the electronic data management system, a communicator for wireless communication with a remote network computer system to enable two-way transfer of data between the network computer system and the electronic data management system
wherein the communicator includes an embedded network server.

3. A portable device for the delivery of medicament comprising
a housing;
received by said housing, a medicament container;
associated with said medicament container, a dispensing mechanism for dispensing medicament from the medicament container;
said portable device further comprising an electronic data management system comprising
    a memory for storage of data concerning use of said portable device;
    a microprocessor for performing operations on said data; and
    a transmitter for transmitting a signal relating to the data or the outcome of an operation on the data; and
associated with the electronic data management system, a communicator for wireless communication with a remote network computer system to enable two-way transfer of data between the network computer system and the electronic data management system
wherein the communicator communicates with the network computer system via a second communications device having telecommunications capability.

4. A portable device according to claim 3, wherein the telecommunications device comprises a cellular phone or pager.

5. A portable device according to claim 3, wherein the communicator communicates with the second communications device using spread spectrum radiofrequency signals.

6. A portable device for the delivery of medicament comprising
a housing;
received by said housing, a medicament container;
associated with said medicament container, a dispensing mechanism for dispensing medicament from the medicament container;
said portable device further comprising an electronic data management system comprising
    a memory for storage of data concerning use of said portable device;
    a microprocessor for performing operations on said data; and
    a transmitter for transmitting a signal relating to the data or the outcome of an operation on the data; and
associated with the electronic data management system, a communicator for wireless communication with a remote network computer system to enable two-way transfer of data between the network computer system and the electronic data management system
wherein the network computer system comprises a private access network computer system.

7. A portable device for the delivery of medicament comprising
a housing;
received by said housing, a medicament container;
associated with said medicament container, a dispensing mechanism for dispensing medicament from the medicament container;
said portable device further comprising an electronic data management system comprising
    a memory for storage of data concerning use of said portable device;
    a microprocessor for performing operations on said data; and
    a transmitter for transmitting a signal relating to the data or the outcome of an operation on the data; and
associated with the electronic data management system, a communicator for wireless communication with a remote network computer system to enable two-way transfer of data between the network computer system and the electronic data management system
wherein the communicator enables communication with a user-specific network address in the network computer system
wherein the user-specific network address is selected from the group consisting of a web-site address, an e-mail address and a file transfer protocol address.

8. A portable device for the delivery of medicament comprising
a housing;
received by said housing, a medicament container;
associated with said medicament container, a dispensing mechanism for dispensing medicament from the medicament container;
said portable device further comprising an electronic data management system comprising
    a memory for storage of data concerning use of said portable device;
    a microprocessor for performing operations on said data; and
    a transmitter for transmitting a signal relating to the data or the outcome of an operation on the data; and
associated with the electronic data management system, a communicator for wireless communication with a remote network computer system to enable two-way transfer of data between the network computer system and the electronic data management system
wherein the communicator enables communication with a user-specific network address in the network computer system
wherein the user-specific network address is accessible to a remote information source such that information from said remote information source can be made available to said user-specific network address.

9. A portable device according to claim 8, wherein information from the user-specific network address can be made available to the remote information source.

10. A portable device according to claim 8, wherein the remote information source is a medicament prescriber.

11. A portable device according to claim 8, wherein the remote information source is a pharmacy.

12. A portable device according to claim 8, wherein the remote information source is an emergency assistance provider.

13. A portable device according to claim 8, wherein the remote information source is a manufacturer of medicament or medicament delivery systems.

14. A portable device according to claim 8, wherein the remote information source is a research establishment.

15. A portable device according to claim 8, wherein the remote information source is an environmental monitoring station.

16. A portable device for the delivery of medicament comprising
   a housing;
   received by said housing, a medicament container;
   associated with said medicament container, a dispensing mechanism for dispensing medicament from the medicament container;
   said portable device further comprising an electronic data management system comprising
      a memory for storage of data concerning use of said portable device;
      a microprocessor for performing operations on said data; and
      a transmitter for transmitting a signal relating to the data or the outcome of an operation on the data; and
   associated with the electronic data management system, a communicator for wireless communication with a remote network computer system to enable two-way transfer of data between the network computer system and the electronic data management system
   additionally comprising a datalink for linking to a local data store to enable communication of data between the local data store and the microprocessor.

17. A portable device according to claim 16, wherein the datalink comprises an infrared emitter and sensor.

18. A portable device according to claim 16, wherein the local data store comprises a personal computer or set-top box.

19. A portable device for the delivery of medicament comprising
   a housing;
   received by said housing, a medicament container;
   associated with said medicament container, a dispensing mechanism for dispensing medicament from the medicament container;
   said portable device further comprising an electronic data management system comprising
      a memory for storage of data concerning use of said portable device;
      a microprocessor for performing operations on said data; and
      a transmitter for transmitting a signal relating to the data or the outcome of an operator on the data; and
   associated with the electronic data management system, a communicator for wireless communication with a remote network computer system to enable two-way transfer of data between the network computer system and the electronic data management system
   additionally comprising a data input system for user input of data to the electronic data management system.

20. A portable device according to claim 19, wherein said data input system comprises a man machine interface selected from the group consisting of a keypad, voice recognition interface, graphical user interface (GUI) or biometrics interface.

21. A portable device for the delivery of medicament comprising
   a housing;
   received by said housing, a medicament container;
   associated with said medicament container, a dispenser mechanism for dispensing medicament from the medicament container;
   said portable device further comprising an electronic data management system comprising
      a memory for storage of data concerning use of said portable device;
      a microprocessor for performing operations on said data; and
      a transmitter for transmitting a signal relating to the data or the outcome of an operation on the data; and
   associated with the electronic data management system, a communicator for wireless communication with a remote network computer system to enable two-way transfer of data between the network computer system and the electronic data management system
   wherein said electronic data management system includes a predictive algorithm or look-up table for calculating the optimum amount of medicament to dispense.

22. A portable device according to claim 21, wherein the memory includes a dose memory for storing dosage data and reference is made to the dose memory in calculating the optimum amount of medicament to dispense.

23. A portable device for the delivery of medicament comprising
   a housing;
   received by said housing, a medicament container;
   associated with said medicament container, a dispensing mechanism for dispensing medicament from the medicament container;
   said portable device further comprising an electronic data management system comprising
      a memory for storage of data concerning use of said portable device;
      a microprocessor for performing operations on said data; and
      a transmitter for transmitting a signal relating to the data or the outcome of an operation on the data; and
   associated with the electronic data management system, a communicator for wireless communication with a remote network computer system to enable two-way transfer of data between the network computer system and the electronic data management system
   additionally comprising a geographic positioning system.

24. A portable device for the delivery of medicament comprising
   a housing;
   received by said housing, a medicament container;
   associated with said medicament container, a dispensing mechanism for dispensing medicament from the medicament container;
   said portable device further comprising an electronic data management system comprising
      a memory for storage of data concerning use of said portable device;
      a microprocessor for performing operations on said data; and
      a transmitter for transmitting a signal relating to the data or the outcome of an operation on the data; and
   associated with the electronic data management system, a communicator for wireless communication with a remote network commuter system to enable two-way transfer of data between the network computer system and the electronic data management system
   additionally comprising a sensor which senses the breath of a user, wherein the sensor communicates breath data to the electronic data management system, wherein said sensor comprises a breath-movable element which is movable in response to the breath of a patient.

25. A portable device according to claim 24, wherein said breath-movable element is selected from the group consisting of a vane, a sail, a piston and an impeller.

26. A portable device for the delivery of medicament comprising
a housing;
received by said housing, a medicament container;
associated with said medicament container, a dispensing mechanism for dispensing medicament from the medicament container;
said portable device further comprising an electronic data management system comprising
a memory for storage of data concerning use of said portable device;
a microprocessor for performing operations on said data; and
a transmitter for transmitting a signal relating to the data or the outcome of an operation on the data; and
associated with the electronic data management system, a communicator for wireless communication with a remote network computer system to enable two-way transfer of data between the network computer system and the electronic data management system
additionally comprising a sensor which senses the breath of a user, wherein the sensor communicates breath data to the electronic data management system, wherein the sensor comprises a pressure sensor for sensing the pressure profile associated with the breath of a user.

27. A portable device for the delivery of medicament comprising
a housing;
received by said housing, a medicament container;
associated with said medicament container, a dispensing mechanism for dispensing medicament from the medicament container;
said portable device further comprising an electronic data management system comprising
a memory for storage of data concerning use of said portable device;
a microprocessor for performing operations on said data; and
a transmitter for transmitting a signal relating to the data or the outcome of an operation on the data; and
associated with the electronic data management system, a communicator for wireless communication with a remote network computer system to enable two-way transfer of data between the network computer system and the electronic data management system
additionally comprising a sensor which senses the breath of a user, wherein the sensor communicates breath data to the electronic data management system, wherein the sensor comprises a moisture sensor for sensing the moisture profile associated with the breath of a user.

28. A portable device for the delivery of medicament comprising
a housing;
received by said housing, a medicament container;
associated with said medicament container, a dispensing mechanism for dispensing medicament from the medicament container;
said portable device further comprising an electronic data management system comprising
a memory for storage of data concerning use of said portable device;
a microprocessor for performing operations on said data; and
a transmitting for transmitting a signal relating to the data or the outcome of an operation on the data; and
associated with the electronic data management system, a communicator for wireless communication with a remote network computer system to enable two-way transfer of data between the network computer system and the electronic data management system
additionally comprising a sensor which senses the breath of a user, wherein the sensor communicates breath data to the electronic data management system, wherein the sensor comprises a gas sensor for sensing the oxygen or carbon dioxide profile associated with the breath of a user.

29. A portable device for the delivery of medicament comprising
a housing;
received by said housing, a medicament container;
associated with said medicament container, a dispensing mechanism for dispensing medicament from the medicament container;
said portable device further comprising an electronic data management system comprising
a memory for storage of data concerning use of said portable device;
a microprocessor for performing operations on said data; and
a transmitter for transmitting a signal relating to the data or the outcome of an operation on the data; and
associated with the electronic data management system, a communicator for wireless communication with a remote network computer system to enable two-way transfer of data between the network computer system and the electronic data management system
additionally comprising a sensor which senses the breath of a user, wherein the sensor communicates breath data to the electronic data management system, wherein said breath data includes breath cycle data.

30. A portable device for the delivery of medicament comprising
a housing;
received by said housing, a medicament container;
associated with said medicament container, a dispensing mechanism for dispensing medicament from the medicament container;
said portable device further comprising an electronic data management system comprising
a memory for storage of data concerning use of said portable device;
a microprocessor for performing operations on said data; and
a transmitter for transmitting a signal relating to the data or the outcome of an operation on the data; and
associated with the electronic data management system, a communicator for wireless communication with a remote network computer system to enable two-way transfer of data between the network computer system and the electronic data management system
additionally comprising a sensor which senses the breath of a user, wherein the sensor communicates breath data to the electronic data management system, wherein said breath data includes peak flow data.

31. A portable device for the delivery of medicament comprising
a housing;
received by said housing, a medicament container;

associated with said medicament container, a dispensing mechanism for dispensing medicament from the medicament container;

said portable device further comprising an electronic data management system comprising
- a memory for storage of data concerning use of said portable device;
- a microprocessor for performing operations on said data; and
- a transmitter for transmitting a signal relating to the data or the outcome of an operation on the data; and associated with the electronic data management system, a communicator for wireless communication with a remote network computer system to enable two-way transfer of data between the network computer system and the electronic data management system additionally comprising a sensor which senses the breath of a user, wherein the sensor communicates breath data to the electronic data management system, additionally comprising an actuator for actuating the dispensing mechanism, said actuator being actuable in response to a trigger signal from the transmitter.

32. A portable device according to claim 31, wherein the electronic data management system includes a predictive algorithm or look-up table for deriving from the breath data when to transmit the trigger signal.

33. A portable device according to claim 31, wherein said actuator comprises an energy store for storing energy which energy is releasable to actuate the dispensing mechanism of the medicament container.

* * * * *